United States Patent
Sun et al.

(10) Patent No.: US 11,761,814 B2
(45) Date of Patent: Sep. 19, 2023

(54) NUTRITIONAL VALUE PREDICTION SYSTEM AND METHOD

(71) Applicant: KONINKLIJKE PHILIPS N.V., Eindhoven (NL)

(72) Inventors: Wen Sun, Shanghai (CN); Qiao Hua, Deyang (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 795 days.

(21) Appl. No.: 16/467,539

(22) PCT Filed: Dec. 15, 2017

(86) PCT No.: PCT/EP2017/083181
§ 371 (c)(1),
(2) Date: Jun. 7, 2019

(87) PCT Pub. No.: WO2018/109221
PCT Pub. Date: Jun. 21, 2018

(65) Prior Publication Data
US 2019/0323879 A1 Oct. 24, 2019

(30) Foreign Application Priority Data

Dec. 15, 2016 (WO) ............................... 2016000684
Mar. 21, 2017 (EP) .................................... 17161969

(51) Int. Cl.
*G01G 19/414* (2006.01)
*G16H 20/60* (2018.01)

(52) U.S. Cl.
CPC ......... *G01G 19/4146* (2013.01); *G16H 20/60* (2018.01)

(58) Field of Classification Search
CPC .......................... G01G 19/4146; G16H 20/60
See application file for complete search history.

(56) References Cited

U.S. PATENT DOCUMENTS

| | | | |
|---|---|---|---|
| 4,481,394 A * | 11/1984 | Tanabe ................. | H05B 6/6482 219/685 |
| 8,330,057 B2 | 12/2012 | Sharawi et al. | |
| 9,702,858 B1 * | 7/2017 | Minvielle ............. | A47J 36/321 |
| 2008/0102175 A1 | 5/2008 | Jeon | |
| 2011/0109301 A1 * | 5/2011 | Johnson ................... | G01R 1/22 324/126 |
| 2014/0170275 A1 | 6/2014 | Bordin | |
| 2015/0305564 A1 | 10/2015 | Jimenez | |

(Continued)

FOREIGN PATENT DOCUMENTS

WO WO2013/108046 * 7/2013 ......... H01R 13/6683

OTHER PUBLICATIONS

International Search Report and Written Opinion dated Feb. 1, 2018 for International Application PCT/EP2017/083181 filed Dec. 15, 2017.

*Primary Examiner* — Natalie Huls
(74) *Attorney, Agent, or Firm* — Maschoff Brennan

(57) ABSTRACT

The invention provides a nutritional value prediction system. A nutritional value of processed food is predicted based on an identity of food to be processed and processing characteristics of a kitchen appliance used to process the food to be processed. Processing characteristics of the kitchen appliance are determined based on a sensed parameter of a power supply of the kitchen appliance.

14 Claims, 6 Drawing Sheets

(56) References Cited

U.S. PATENT DOCUMENTS

| | | |
|---|---|---|
| 2016/0174748 A1 | 6/2016 | Baldwin |
| 2016/0327281 A1 | 11/2016 | Bhogal |
| 2016/0350704 A1 | 12/2016 | Minvielle |
| 2018/0063900 A1* | 3/2018 | Minvielle ............... A23L 3/003 |
| 2021/0037611 A1* | 2/2021 | Luckhardt ............ H05B 1/0258 |

* cited by examiner

NUTRITIONAL VALUE PREDICTION SYSTEM AND METHOD

CROSS REFERENCE TO RELATED APPLICATIONS

This application is the U.S. National Phase application under 35 U.S.C. § 371 of International Application No. PCT/EP2017/083181 filed Dec. 15, 2017, published as WO 2018/109221 on Jun. 21, 2018, which claims the benefit of European Patent Application Number 17161969.5 filed Mar. 21, 2017 and Patent Application Number PCT/CN2016/000684 filed Dec. 15, 2016. These applications are hereby incorporated by reference herein.

FIELD OF THE INVENTION

This invention relates to the field of nutrition, and in particular to the field of nutritional value prediction systems.

BACKGROUND OF THE INVENTION

Health has been a growing interest in the public conscious, and products that assist people to prepare, cook and eat food in a healthy way have become increasingly relevant and attractive.

In particular, it has been recognised that ensuring an appropriate nutrient intake of a person may significantly contribute to their well-being. However, optimizing a person's nutrient intake is somewhat complicated, as optimal nutrient intake varies according to an individual's physical condition and personalized needs. Indeed, it will be appreciated that optimization of nutrient intake may depend on a variety of factors, such as: gender, life stage, health status, eating habits, individual targets and so on.

In this way, there has been an increasing demand for products which can assist in monitoring nutrient intake.

SUMMARY OF THE INVENTION

The invention is defined by the claims.

According to some examples, there is provided a nutritional value prediction system for predicting a nutritional value of processed food, the system comprising: a food identity determiner adapted to obtain food identity data indicative of an identity of the food to be processed by a kitchen appliance, wherein the kitchen appliance is adapted to process food to be processed into processed food; an appliance characteristic determiner adapted to: sense a parameter of a power supply provided to the kitchen appliance; and determine processing characteristics of the kitchen appliance, indicative of characteristics of the processing performed by the kitchen appliance, based on the sensed parameter of the power supply; and a nutritional value predictor adapted to predict a nutritional value of the processed food based on the determined processing characteristics of the kitchen appliance and the food identity data.

Thus embodiments provide simple and reliable apparatus which can predict a nutritional value of processed food based on information relating to an identity of food to be processed (i.e. what food is to be processed) and an indication of how the identified food is to be processed.

The indication of how the identified food is to be processed corresponds to processing characteristics of a kitchen appliance. The processing characteristics of the kitchen appliance may be obtained by the appliance characteristic determiner which determines the processing characteristics based on a sensed parameter of a power supply to the kitchen appliance.

Determining an identity of the food to be processed enables predetermined nutritional values of that food (e.g. vitamin content) to be obtained. This may increase an ease with which the nutritional value of the processed food is determined, as an accurate measure of the nutritional value of the food prior to processing may be obtained.

A nutritional value of processed food may thereby be readily predicted prior to or during processing of food. This may increase an ease with which an individual assesses their (e.g. potential) nutritional intake.

The system may avoid a need to weigh or otherwise measure the nutritional value of processed food after processing has occurred. Furthermore, embodiments enable an individual to observe the effects of different processing methods (e.g. different operating modes of a kitchen appliance) on nutritional value, providing a greater ease in selecting an appropriate processing method for their needs.

The invention is based at least in part on the recognition that different processing methods, parameters and characteristics may alter the nutritional value of food in different ways. By way of example, food cooked at a first temperature may have a different nutritional value to food cooked at a second temperature. Similarly, food preserved by freezing may have a different nutritional value to food preserved by sealing.

The system may provide a method of obtaining appliance information from presently unconnected kitchen appliances (such as conventional, non-smart ovens and the like) to be used when determining nutritional values of food processed by the said unconnected kitchen appliances. This may enable such unconnected appliances to be integrated into a smart or automated home environment.

The system may further comprise a food quantity determiner adapted to obtain food quantity data indicative of a quantity of food to be processed by the kitchen appliance wherein the nutritional value predictor is adapted to predict the nutritional value of the processed food further based on the food quantity data.

A more accurate measure of a processed food's nutritional value may be obtained by identifying the quantity of food to be processed. By way of example, a first quantity of food may cook more quickly than of a second, larger quantity of food. This would affect the nutritional value of the food to be processed.

The food quantity data may comprise food weight data indicative of a weight of food to be processed, wherein the nutritional value predictor is adapted to predict a nutritional value of the processed food based on at least the determined processing characteristics of the kitchen appliance, the food weight data and the food identity data.

Thus a weight of food (prior to processing) may be used to determine a nutritional value of the food after being processed.

The appliance characteristic determiner may be adapted to sense a current supplied to the kitchen appliance by the power supply and determine the processing characteristics of the kitchen appliance based on the sensed current.

A processing characteristic of the kitchen appliance may be determined based on a current demanded by the kitchen appliance. It is recognised that different kitchen appliances, or different operating modes of a kitchen appliance, are associated with different current demands. In this way, a processing characteristic of the kitchen appliance may be determined.

Detection of a current supplied to a kitchen appliance provides a simple and low-cost method of determining the processing characteristics of the kitchen appliance, with a low power consumption.

Optionally, the appliance characteristic determiner comprises: a parameter sensor adapted to sense the parameter of the power supply; and a characteristic determination arrangement adapted to receive the sensed parameter of the power supply and determine the processing characteristics of the kitchen appliance based on the sensed parameter.

The sensing of a parameter of the power supply and the determination of the processing characteristics of the kitchen appliance may be performed by separate modules of the system. This may provide a more flexible and intuitive system, which may be readily updated.

The appliance characteristic determiner may be adapted to compare the sensed parameter to at least one reference parameter, each reference parameter corresponding to different possible processing characteristics of the kitchen appliance, to determine the processing characteristics of the kitchen appliance.

Thus the appliance characteristic determiner may consult, for example, a database or dataset of reference parameters to identify processing characteristics of the kitchen appliance. Such a database may be housed, for example, externally to the appliance characteristic determiner in a distributed computing network (e.g. cloud computing arrangement) or an external server.

The appliance property determiner may comprise an electrical connector adapted to electrically connect the kitchen appliance to the power supply.

There is provided a concept of a 'smart-plug' which couples the kitchen appliance to the power supply. Such a smart-plug may be adapted to monitor the power supply to the kitchen appliance and provide an easily implementable appliance characteristic determiner with improved user convenience.

The processing characteristics of the kitchen appliance may comprise one or more of the following: a type of the kitchen appliance; an identity of the kitchen appliance; a model of the kitchen appliance; an operating mode of the kitchen appliance; and an operating parameter of the kitchen appliance, such as a temperature at which the food is processed, a humidity at which the food is processed, a time for which food is processed and so on.

Processing characteristics may thereby identify a manner in which the food is processed by the kitchen appliance. This may entail identifying a type of the kitchen appliance, for example, whether a kitchen appliance is a cooker, microwave or freezer. In other or further embodiments, this may include identifying an (active) operating mode, such as a pre-set program of the kitchen appliance or an operating parameter, such as a (current) temperature, of the kitchen appliance.

In particular, different kitchen appliances may be associated with different parameters of a received power supply. Similarly, different operating modes of kitchen appliances, such as different temperatures of an oven, may be associated with different parameters of a received power supply.

Thus, a system may identify various processing characteristics of the kitchen appliance and determine what effect this may have on the nutritional value of food processed by the kitchen appliance having said processing characteristics.

The predicted nutritional value preferably comprises one or more of the following: a number of predicted calories of the processed food; a predicted vitamin content of the processed food; a predicted fat content of the processed food; a predicted mineral content of the processed food; a predicted carbohydrate content of the processed food; a predicted sugar content of the processed food; a predicted protein content of the processed food; a predicted fibre content of the processed food; and a predicted salt content of the processed food.

According to another aspect of the invention, there is provided a method of predicting a nutritional value of processed food, the method comprising: obtaining food identity data indicative of an identity of the food to be processed by a kitchen appliance, wherein the kitchen appliance is adapted to process food to be processed into processed food; sensing a parameter of a power supply provided to the kitchen appliance; determining processing characteristics of the kitchen appliance, indicative of characteristics of the processing performed by the kitchen appliance, based on the sensed parameter of the power supply; and predicting a nutritional value of the processed food based on the determined processing characteristics of the kitchen appliance and the food identity data.

The method may further comprise obtaining food quantity data indicative of a quantity of food to be processed by the kitchen appliance, wherein the predicting a nutritional value of the processed food is further based on the food quantity data.

Optionally, the obtaining food quantity data comprises obtaining food weight data indicative of a weight of the food to be processed, and the predicting a nutritional value of the processed food comprises predicting a nutritional value of the processed food based on at least the determined property of the kitchen appliance and the food weight data.

The step of sensing a parameter of the power supply may comprise sensing a current provided by the power supply to the kitchen appliance.

The method may further comprise comparing the sensed parameter to at least one reference parameter, each reference parameter corresponding to different possible processing characteristics of the kitchen appliance, to determine the processing characteristics of the kitchen appliance.

There is also proposed a computer program comprising code means which is adapted, when said program is run on a computer, to perform any method previously described.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a nutritional value prediction system. A nutritional value of processed food is predicted based on an identity of food to be processed and processing characteristics of a kitchen appliance used to process the food to be processed. Processing characteristics of the kitchen appliance are determined based on a sensed parameter of a power supply of the kitchen appliance.

The proposed embodiments are at least partly based on the realisation that processing characteristics of kitchen appliances are associated with unique signatures or patterns in their electricity consumption. As such, parameters of a power supply provided to a kitchen appliance vary, for example, depending upon an identity of the kitchen appliance and a way in which the kitchen appliance operates. It is also recognised that nutritional values of processed food depend upon the processing characteristics of the kitchen appliances.

Illustrative embodiments may, for example, be employed in smart-home or automated homes. In particular, embodiments may be used to enable parameters of previously unconnected kitchen appliances to be integrated in a network for predicting nutritional values, which may be used to assist in nutrient monitoring in an intuitive and accurate manner.

Reference to food generally refers any nutritious substance, whether in liquid or solid form, or a combination of both. The food to be processed by a kitchen appliance may be comprise food in at least one or more of the following forms: a raw or unprocessed form, such as raw meat or vegetables; a partially processed form, such as blanched vegetables; or a fully processed form, such as cooked meat.

Reference to a kitchen appliance generally refers to any food processing appliance or apparatus which is adapted to process food. Processing food may comprise any one or more of the following: chopping, freezing, liquefying, cooking, freezing, pickling, pasteurizing, preserving, mincing, sealing and so on. Thus, the invention recognises that different methods of processing foods may alter the nutritional value of food in different ways.

Whilst food processing is used to refer to any method of processing food, a "food processor" is used in the conventional manner to refer to a motor-driven appliance commonly used to slice, chop or shred food.

Figure 1:
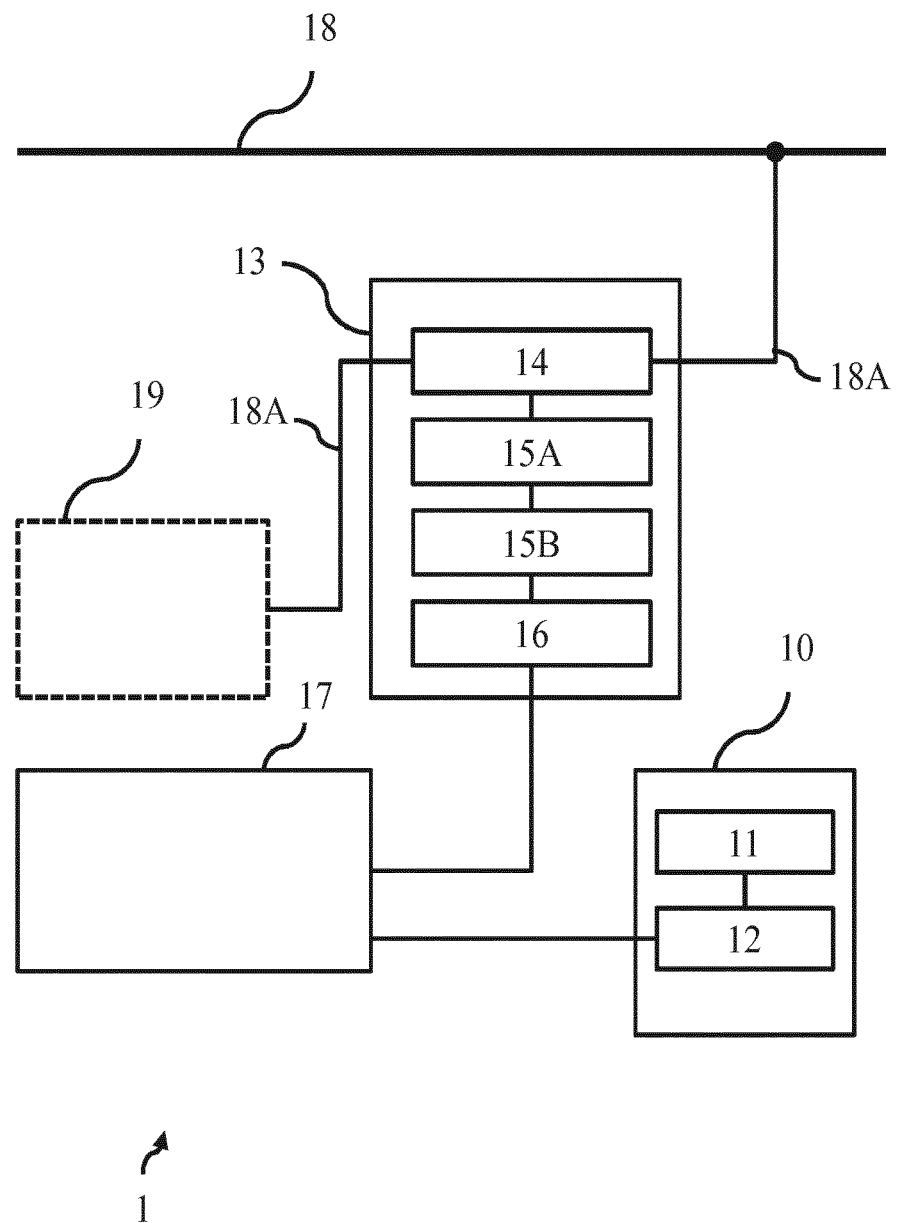
FIG. 1 shows a nutritional value prediction system according to an embodiment.

FIG. 1 illustrates a nutritional value prediction system 1 according to an embodiment. The nutritional value prediction system 1 comprises a food identity determiner 10, an appliance characteristic determiner 13 and a nutritional value predictor 17.

The nutritional value prediction system 1 is adapted to predict a nutritional value of food processed by a kitchen appliance 19. The kitchen appliance 19 is adapted to process food so as to provide processed food.

The nutritional value predictor 17 predicts the nutritional value of the processed food based on food identity data, received from the food identity determiner 10, and processing characteristics of the kitchen appliance, received from the appliance characteristic determiner 14.

For example, the food identity data may be used to determine an initial nutritional value (e.g. using a database) and the processing characteristics may be used to predict how this initial nutritional value changes based on the processing characteristics. In another example, the identity of the food and the processing characteristics may be used together to identify a nutritional value of the processed food (e.g. using a database).

The food identity determiner 10 obtains food identity data indicative of an identity of the food to be processed by the kitchen appliance 19.

For example, the food identity determiner 10 may comprise a food identifier 11, such as a bar-code scanner or a camera arrangement having image recognition capabilities, and a communication arrangement 12 which is adapted to pass the food identity data to the nutritional value predictor 17.

In yet another embodiment, the food identity determiner may comprise a user input unit adapted to receive an input from a user which indicates the identity of the food. For example, the user may interface with a mobile device, e.g. use a mobile app, to provide an identity of the food, which may be received by a food identity determiner.

Food identity data may comprise an indication of the nutritional value of the food to be processed (which is typically unique to that food), an identity of the food to be processed, or information/data which may be subsequently processed to identify the food to be processed.

The appliance characteristic determiner 13 obtains a parameter of a power supply 18A supplied to the kitchen appliance 19, and determines processing characteristics of the kitchen appliance 19 based on the obtained parameter.

For example, the appliance characteristic determiner 13 may comprise an electrical connector 14 adapted to electrically connect the kitchen appliance 19 to a mains power supply 18.

A parameter sensor 15A may sense a parameter of the power supply 18A flowing through the electrical connector 14. For example, the parameter sensor 15A may sense a value of the current flowing through the electrical connector 14.

A characteristic determination arrangement 15B may receive the sensed parameter of the power supply 18A and determine the processing characteristics of the kitchen appliance 19 based on the sensed parameter. For example, the characteristic determination arrangement may compare a sensed parameter to one or more known parameter (each associated with different sets of one or more processing characteristics) and determine that the processing characteristics comprise a particular set of processing characteristics based on this comparison.

It has been recognized that many kitchen appliances, and operating modes of such kitchen appliances, have a unique signature in their electricity consumption patterns (e.g. current drawn, superimposed voltage pattern on top of the regular AC pattern, etc.). The appliance characteristic determiner 13 may thereby identify a kitchen appliance and processing characteristics thereof by detecting this unique signature.

The appliance characteristic determiner 13 may further comprise a communication arrangement 16 to pass the processing characteristics to the nutritional value predictor 17.

The appliance characteristic determiner 13 may be considered as a 'smart-plug' which may be connected between a plug of a kitchen appliance and a socket of a typical mains power supply, such as a domestic outlet or socket. This provides an easy to implement module capable of determining processing characteristics of a kitchen appliance.

By using food identity data and processing characteristics of the kitchen appliance 19, a nutritional value of the processed food may be reliably and accurately obtained.

By using an appliance characteristic determiner 13, which is adapted to determine processing characteristics of a kitchen appliance 19 based on a parameter of a power supply, kitchen appliances not currently capable of passing processing characteristics may be connected into a nutritional value prediction system. Thus, a kitchen appliance does not require communicative capabilities, as this may be provided by the (external) appliance characteristic determiner.

The communication arrangements 16, 19 of the food identity determiner 10 and the appliance characteristic determiner 13 may, in particular, comprise a wireless communication unit to communicate with the nutritional value predictor. Suitable wireless communication protocols that may be used to communicate with the appliance characteristic determiner include an infrared link, ZigBee, Bluetooth, a wireless local area network protocol such as in accordance with the IEEE 802.11 standards, a 2G, 3G or 4G telecommunication protocol, and so on. Other formats will be readily apparent to the person skilled in the art. Preferably, the communication arrangements operate using a ZigBee protocol, as this provide a low cost, wireless connection. The skilled person would also understand that the communication arrangements may communicate using a wired communication protocol.

Processing characteristics are the properties of a kitchen appliance 19, or properties of a current operating mode of the kitchen appliance, which may affect the nutritional value of food processed by that kitchen appliance. It is recognised that different kitchen appliances affect the nutritional value in different ways, and that a same kitchen appliance may be operated in different modes to influence the nutritional value of the processed food.

By way of example only, processing characteristics of a kitchen appliance, being properties which affect the nutritional value of processed food, may comprise at least one of the following: an identity of the kitchen appliance; a model of the kitchen appliance; an operating mode of the kitchen appliance; and an operating parameter of the kitchen appliance, such as a temperature at which the food is processed, a humidity at which the food is processed, a time for which food is processed and so on.

It is recognised that a wide variety of different nutritional parameters or properties may be affected by the manner in which food is processed. For example, a nutritional value may be at least one of: a number of predicted calories of the processed food, a predicted vitamin content of the processed food, a predicted fat content of the processed food, a predicted mineral content of the processed food; a predicted carbohydrate content of the processed food; a predicted sugar content of the processed food; a predicted protein content of the processed food; a predicted fibre content of the processed food; and a predicted salt content of the processed food.

It will be readily apparent that more than one nutritional value (e.g. corresponding to different nutritional parameters) may be generated.

Figure 2:
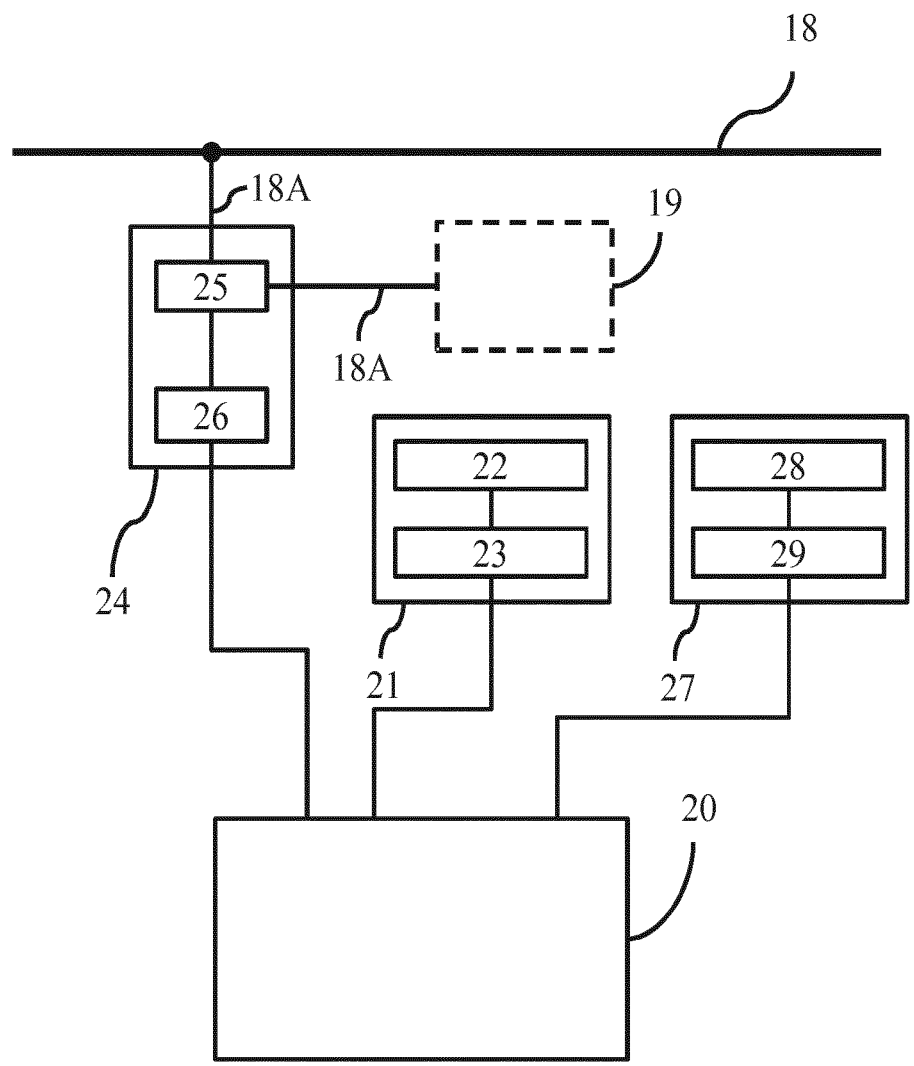
FIG. 2 illustrates a nutritional value prediction system according to another embodiment.

FIG. 2 illustrates a nutritional value prediction system 2 according to an embodiment. The nutritional value prediction system 2 comprises a food identity determiner 21, a parameter sensor 24 and a food quantity determiner 27.

A processing arrangement 20 of the system 2 is adapted to predict a nutritional value based on food identity data, received from the food identity determiner 21, a parameter of the power supply, received from the parameter sensor 24, and food quantity data, received from the food quantity determiner 27.

The food identity determiner may comprise a food identifier 22 adapted to generate food identity data, and a communication arrangement 23 for passing the food identity data to the processing arrangement 20.

In some embodiments, the food identity determiner 21 may operate, for example, substantially as described with reference to FIG. 1.

In other embodiments, rather than the food identity determiner 21 itself determining an identification of the food to be proceed, the generated food identity data may enable subsequent identification of the food to be processed. For example, the food identity data may comprise image data (e.g. a picture of the food) or bar-code information. The processing arrangement 20 may receive the food identity data and determine an identity of the food based on the received food identity data. This allows for a simpler and cheaper method of identifying the food to be processed, as a potentially complex processing arrangement need not be positioned within the food identity determiner.

The parameter sensor 24 is adapted to sense a parameter of the power supply 18A, provided from a mains supply 18, for the kitchen appliance 19. In embodiments, the parameter sensor comprises an electrical connector 25 which connects a kitchen appliance to the mains supply. In other embodiments, the sensor may comprise a passive sensor adapted to monitor one or parameter of the power supply, for example it may be adapted to clip onto a wire carrying power for the kitchen appliance and monitor an electromagnetic field generated by the wire.

The parameter sensor 24 passes the parameter of the power supply 18A to the processing arrangement 20 via a communication arrangement 26.

The food quantity determiner 27 may comprise food scales 28, adapted to weigh a quantity of food to be processed so as to generate food weight data, and a communication arrangement 29 adapted to pass the food weight data to the processing arrangement. Thus, the food quantity determiner generates food quantity data comprising at least food weight data.

In other embodiments, the food quantity determiner may comprise other measuring tools, such as a spaghetti measurer or egg counter. Thus, the food quantity data may comprise an indication of how many units of a particular food are to be processed. In yet another embodiment, the food quantity data may comprise an indication of the cut size of the food to be processed, for example, an indication of how the food to be processed has been cut according to a culinary knife cut (e.g. dicing, brunoising etc.).

In yet other or further embodiments, the food quantity data may be provided by a user via a connected mobile device, for example, using a mobile app.

Figure 3:
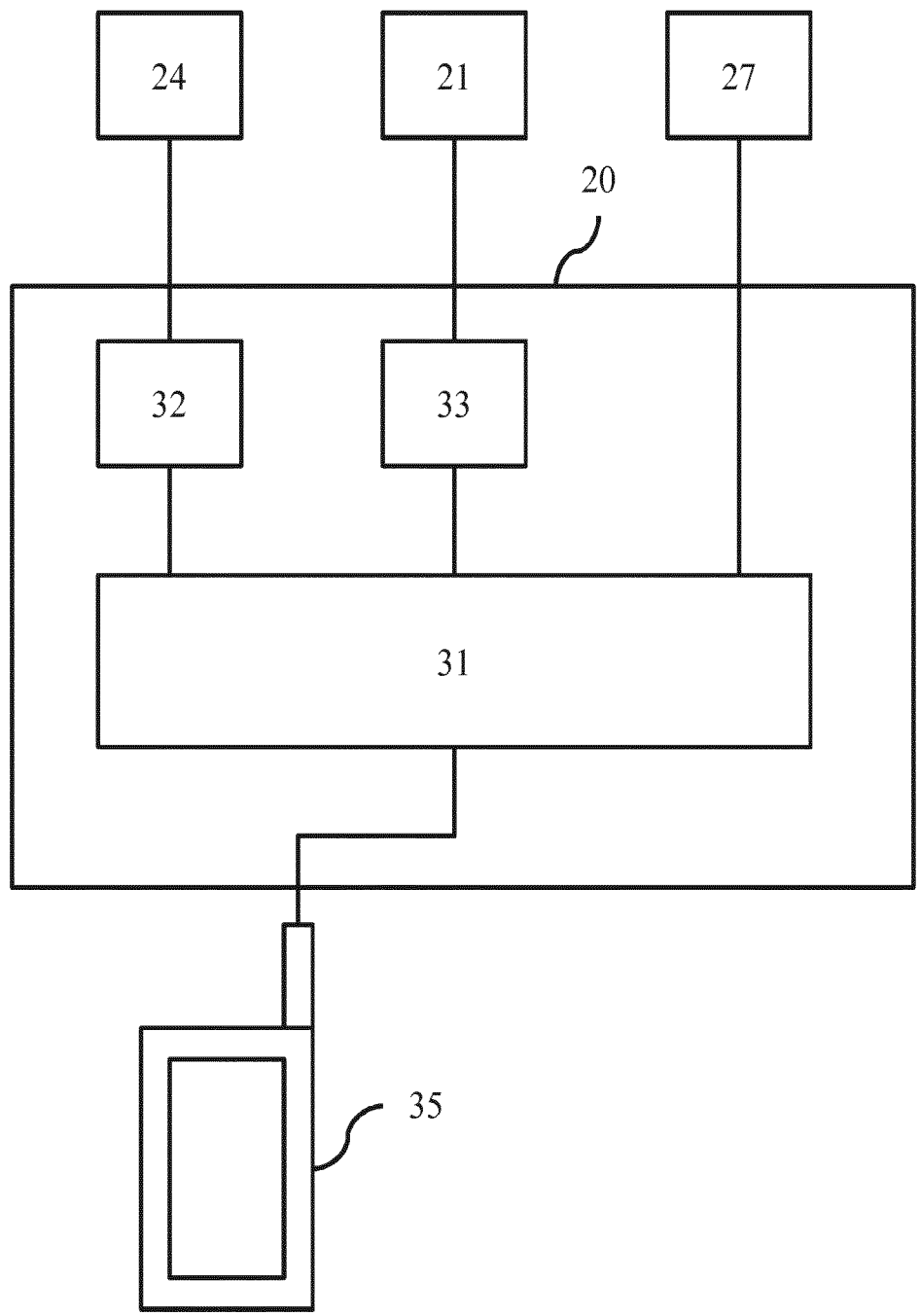
FIG. 3 illustrates a processing arrangement of a nutritional value prediction system according to an embodiment.

FIG. 3 illustrates the processing arrangement 20 according to an embodiment. The processing arrangement 20 comprises a nutritional value predictor 31 which is adapted to predict a nutritional value of the processed food.

The processing arrangement 20 may be adapted to communicate with a user interface arrangement 35, which may comprise a mobile device or other computing device. The processing arrangement 20 may be adapted to provide the user interface arrangement 35 with the predicted nutritional value or other information (such as the food identity data).

The processing arrangement 20 also comprises a characteristic determination arrangement 32 adapted to determine the processing characteristics of the kitchen appliance based on the sensed parameter, received from the parameter sensor 24.

As briefly described previously, kitchen appliances, and operating modes of such kitchen appliances, have a unique signature in their electricity consumption patterns. The characteristic determination arrangement may be adapted to monitor the parameter of the power supply in order to identify the kitchen appliance or an operating mode of the kitchen appliance.

For example, the sensed parameter may be an average current supplied to the kitchen appliance 19, and the characteristic determination arrangement 32 may be adapted to identify processing characteristics of the kitchen appliance based on the sensed average current. The processing characteristics may comprise, for example, an identity of the kitchen appliance and/or an operating mode of the kitchen appliance.

In particular embodiments, a value of a sensed parameter of the power supply provided to the kitchen appliance may be compared to values of reference parameters of known power demands of kitchen appliances operating in different operating modes. Thus, a sensed parameter may be compared to one or more reference parameters, each reference parameter being associated with a set of one or more different operating characteristics.

For example, a first reference parameter may be associated with a first set of operating characteristics, and a second reference parameter may be associated with a second set of operating characteristics.

Table 1 illustrates an example of how processing characteristics of a kitchen appliance may be determined based on a detected average current of a power supply provided to the kitchen appliance (i.e. the average current demanded by the kitchen appliance). In particular, Table 1 illustrates a database or look-up table of characteristics of a power supply drawn by various kitchen appliances in various operating modes Appliances A and C may be operable in a plurality of modes, whereas an Appliance B may be operable in only a single mode. Each mode of Appliances A and C is associated with a different average current demand, such that an identity of the appliance (e.g. A, B or C) and an operating of said appliances may be readily identified based on the average current demanded by the appliance. Thus, processing characteristics of the kitchen appliance (which processes food to be processed) may be easily obtained by referring to the database or lookup table, such as that illustrated by Table 1.

For example, if an average current demanded by the kitchen appliance falls between 3A and 4A, it may be determined that an identity of the kitchen appliance is A. If an average current demanded by the kitchen appliance falls between 3.45 and 3.55, the operating mode (of the identified kitchen appliance) may be identified as 1.

Thus it can be seen that a set of operating characteristics (here, appliance identity and operating mode) may be identified based on a comparison between the sensed parameter of the power supply and a reference parameter.

TABLE 1

| Appliance Appliance Identity | Operating Mode | Power Supply Average Current (A) | Characteristics of Current |
|---|---|---|---|
| A | 1 | 3.50 | Direct |
|   | 2 | 3.91 | Direct |
| B | N/A | 6.05 | Pulsating |
| C | 1 | 6.17 | Alternating |
|   | 2 | 6.61 | Alternating |
|   | 3 | 6.95 | Alternating |

When comparing the sensed parameter to one or more reference parameters, the characteristic determination arrangement may identify whether a value of the sensed parameter falls within a predetermined range of a value of the reference parameter (e.g. ±2% or ±0.1A).

In at least one embodiment, in the event that the sensed parameter may be associable with more than one reference parameter (and thereby more than one set of processing characteristics), the characteristic determination arrangement may select the closest reference parameter (and corresponding set of processing characteristics).

In another embodiment, the processing arrangement may provide a user (e.g. via the user interface arrangement 35) with a list of possible processing characteristics, and ask a user to select a set of processing characteristics. For example, with reference to Table 1, if an average current demanded by the kitchen appliance is 6.10A, the characteristic determination arrangement 32 may determine that the processing characteristics of the kitchen appliance is either "Appliance Identity=B" or "Appliance Identity=C, Operating Mode=1". The processing characteristic may subsequently ask the user to select the appropriate processing characteristics of the appliance. This selection may be stored for future reference.

In yet another embodiment, the characteristic determination arrangement 32 may be adapted to identify the appropriate set of processing characteristics based on further parameters of the power supply 18A provided to the kitchen appliance 19. By way of example, the characteristic determination arrangement may determine processing characteristics further based on a voltage, voltage pattern or current pattern demanded by the kitchen appliance (i.e. of the power supply provided to the kitchen appliance). Thus processing characteristics of a kitchen appliance may be determined based on two or more parameters of the power supply provided to the kitchen appliance.

In a particular example, the characteristics determination arrangement 32 may be adapted to identify the set of processing characteristics based on a pattern of the current provided by the power supply. For example, with reference to Table 1, if it is determined based on an average current demand that the processing characteristics of the kitchen appliance comprises either "Appliance Identity=B" or "Appliance Identity=C, Operating Mode=1", the characteristics determination arrangement 32 may identify a characteristic of the current provided to the kitchen appliance to determine the appropriate processing characteristics. Thus, if the power supply is associated with a pulsating current, the processing characteristics will be identified as "Appliance Identity=B", whereas if the power supply is associated with an alternating current, the processing characteristics will be identified as "Appliance Identity=C, Operating Mode=1".

Figure 4:
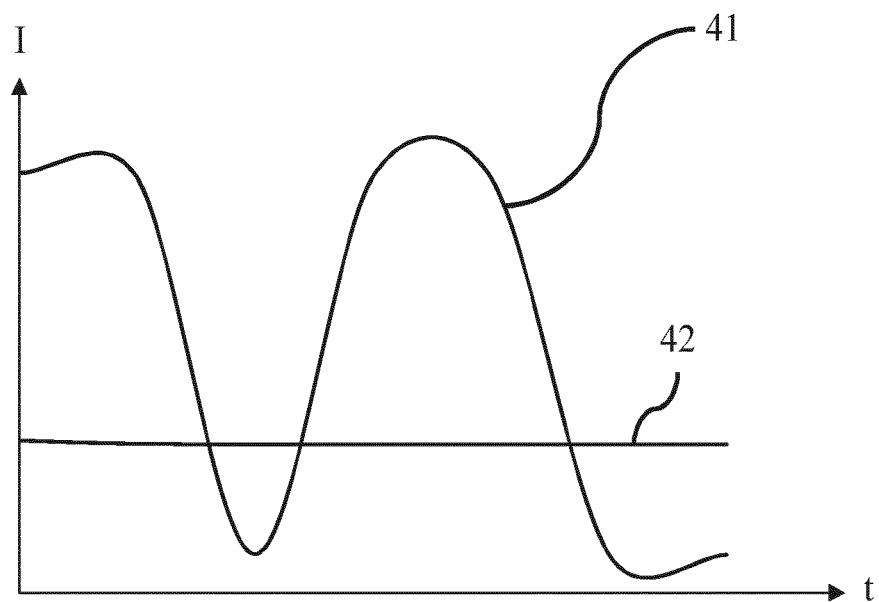
FIG. 4 illustrates current-time profiles of a power supply provided to a first and second kitchen appliance.

Such an embodiment may be more readily understood with further reference to FIG. 4, which illustrates current-time profiles of a power supply provided to a first and second kitchen appliance.

In particular FIG. 4 identifies a first current-time profile 41 of a power supply for a first kitchen appliance associated with a first set of processing characteristics, and a second current-time profile 42 for a second kitchen appliance associated with a second set of processing characteristics. It will be apparent that the current-time profile associated with each set of processing characteristics is different.

Based on the characteristics of the current-time profile, that is a pattern of the current provided by the power supply, processing characteristics of a kitchen appliance may be readily identified. For example, if a current-time profile of a power drawn by the kitchen appliance is determined to be an alternating current, then the processing characteristics of the first kitchen appliance will be selected as the appropriate processing characteristics.

Thus, a plurality of reference sets of one or more power characteristics of the power drawn by the kitchen appliance are each associated with a set of one or more processing characteristics of the kitchen appliance. The reference set of power characteristics most closely matching a sensed set of power characteristics may be selected, and the associated processing characteristics identified.

In particular embodiments, a current-time profile of the power supply 18A is measured, and compared to known current-time profiles associated with different sets of processing characteristics. The set of processing characteristics, having a current-time profile that most closely matches the measured current-time profile, may thereby be selected. Other patterns of the power supply may be used in a similar fashion (e.g. voltage-time profile or power-time profile).

In some other examples, a history or memory of a parameter of a power supply (e.g. how long a particular parameter has been at a particular value) may be used to determine processing characteristics. For example, a fridge may be associated with a same current demand for a long period of time (e.g. more than a day), as a current demand of the fridge will likely be constant and stable, whereas a cooker would not be associated with a same current demand for a same period of time.

Thus, a characteristic determination system may be able to distinguish between kitchen appliances and/or operating parameters based on a length of time for which a value of a given power supply parameter is substantially the same.

In some embodiments, the characteristic determination arrangement may employ pattern recognition of a power supply parameter to identify processing characteristics of the kitchen appliance. By way of example, a particular kitchen appliance may be associated with start-up routine that requests a specific pattern of current or voltage, which may be recognised by the system. Thus, a pattern of change in a particular parameter may be detected and correlated to appropriate processing characteristics of the kitchen appliance.

In at least one embodiment, a database or lookup table used by the characteristic determination arrangement 32 (such as that illustrated by Table 1) may be defined by a user or individual. For example, a user may provide the characteristic determination arrangement 32 with an identity of each appliance in a particular location (home, office, kitchen and so on). The characteristic determination arrangement may compile a database comprising details of processing characteristics (based on the user input) and reference parameters associated with each identified appliance (e.g. based on sensed parameters of the power supply drawn by the identified appliance, or obtained from a database containing processing characteristics of the identified appliance).

For example, a user may indicate that a particular location contains a cooker (having a particular serial or model number) and a microwave (having another particular serial or model number). A database or dataset comprising sets of reference parameters, each associated with various operating modes of each appliance, may be compiled, where each set of reference parameters are associated with a set of processing characteristics.

In at least one embodiment, in the event that the characteristic determination arrangement 32 is unable to identify the processing characteristics of the kitchen appliance 19, the nutritional value prediction system is adapted to request a user to input (e.g. via the user interface arrangement 35) processing characteristics for use by the nutritional value prediction system. In other embodiments, if a user detects that the detected processing characteristics are incorrect (e.g. an incorrect kitchen appliance is identified), the user may input the correct processing characteristics for use by the nutritional value prediction system.

The processing characteristics input by the user may be stored in the database, alongside the sensed parameters of the power supply 18A, for future reference by the characteristic determination arrangement, or a characteristic determination arrangement of another nutritional value prediction system. Thus, information about processing characteristics may be gathered, associated with particular parameters of a demanded power supply, and used to populate a database or dataset with reference parameters.

In this way, a database may advantageously be compiled using 'crowd-sourced' information. This enables a quick and accurate way of compiling a database of reference parameters for particular processing characteristics, to enable improved accuracy in identifying the processing characteristics based on a sensed parameter.

Although embodiments generally refer to a current of a power supply provided to a kitchen appliance, it will be apparent that other parameters of the power supply may be used to identify processing characteristics of the kitchen appliance to particular advantage. For example, a power demanded by the kitchen appliance, a characteristic of an electromagnetic field output by a wire carrying the power supply, a pattern of current demand and so on.

In some embodiments, the characteristic determination arrangement may employ pattern recognition of power supply parameter to identify processing characteristics of the kitchen appliance. By way of example, a particular kitchen appliance may be associated with start-up routine that requests a specific pattern of current or voltage, which may be recognised by the system. Thus, a pattern of change in a particular parameter may be detected and correlated to appropriate processing characteristics of the kitchen appliance.

With continued reference to FIG. 3, the processing arrangement 20 also comprises a food identifying unit 33 adapted to identify the food to be processed.

In particular, the food identifying unit 33 may receive food identity data from the food identifier 21, and determine an identity of the food to be processed based on the food identity data.

By way of example, the food identity data may comprise barcode information which may be used by the food identification unit 33 to identify the food to be processed, for example by consulting a database. In another example, the food identity data comprises a picture (i.e. image data) of the food be processed, and the food identification unit 33 may use an image processing method in order to identify the food in the picture. In this way, the food identification unit 33 may consult a database in order to identify the food to be processed.

In yet another embodiment, the food identifier 21 may represent an input module which allows the user to directly input an identity of the food to be processed. In particular embodiments, the food identifier is comprised as an aspect of the user interface arrangement 35. Thus, an identity of the food may be directly input by a user, for example, using an application for a mobile device.

In yet another embodiment, the food identification unit may obtain nutritional information about food to be processed. For example, this may comprise looking up nutritional information of the food to be processed in a database or look-up table. This may provide an increased accuracy in identifying the nutritional value of the food processed by the kitchen appliance, as an initial nutritional value may be readily obtained.

Other methods of generating food identity data or otherwise identifying the food to be processed will be apparent to the person skilled in the art.

Based upon the identity of the food to be processed, food quantity (received from the food quantity determiner 27) and the processing characteristics, the nutritional value predictor predicts a nutritional value of the food processed by the kitchen appliance 19.

The present invention recognises that processing characteristics of the kitchen appliance may adjust the weight loss and/or the nutritional content, and thereby the nutritional value, of processed food. By way of example, a higher humidity may result in less weight loss than a lower humidity for a cooker or oven.

For example, a nutrient amount of the processed food may be calculated based on weight before processing, a predicted weight loss (caused by the processing) and a known nutritional concentration of the identified food after cooking.

In particular embodiments, the final nutritional value (of the processed food) is calculated as being equal to the nutritional concentration multiplied by the food weight after processing.

Nutritional concentration of the processed food may be obtained from an available database, such as one of the USDA Food Composition Databases, according to food type and the processing characteristics. These databases may refer to the data of a general 'processed' status of food. For example, the databases may provide a general 'cooked' status of food.

The food weight of the processed food is equal to the weight retention rate (w) multiplied by the weight of the food prior to processing. For some food processing methods, such as boiling, steaming or blending, it is recognised that the food processing does not significantly change food weight. In these cases, the weight retention weight w can be set as 1. In particular, it is recognised that typically 'wet cooking' methods do not significantly alter the weight of the food.

For other food processing methods, such as dry cooking methods including air frying or oven baking, the weight retention rate may be determined by a function of cooking time, temperature and humidity. Generally speaking, the weight retention rate may thereby be calculated based of the processing characteristics of the kitchen appliance.

Furthermore, a modified equation can be used to improve the accuracy of the estimation. For example, the final nutritional value may be calculated as the product of: a retention factor r, a nutritional concentration of the processed food (or of the food to be processed) and a food weight after processing, which may be calculated as previously described.

Here the retention factor r (or coefficient factor) reflects the variations on nutrient retention rate for food processed by a kitchen appliance having particular processing characteristics.

By way of example, for evaluating a nutritional value associated with a macronutrient, such as fat, carbohydrate, protein or possibly calories, retention factor r may be set to 1, as retention of such macronutrients is typically very high following food processing. For evaluation of a nutritional value associated with a micronutrient (such as vitamins or minerals), retention factor r can be derived using a variety of different approaches.

For example, a retention factor may be obtained from a national database, such as the USDA Table of Nutrient Retention Factors. In particular, a retention factor may be identified according to food group (e.g. food identity data) and processing characteristics identified. By way of example, and with reference to this USDA table, a retention factor for a nutritional value of vitamin C of potato cooked according to a frying process is 80% (i.e. 0.8), whereas a retention factor for a nutritional value of vitamin C for potato cooked according to a mashing process is 75% (i.e. 0.75).

By way of another example: retention factor r can be specifically determined for a cooking process as a function of cooking parameters (e.g. time and temperature).

Figure 5:
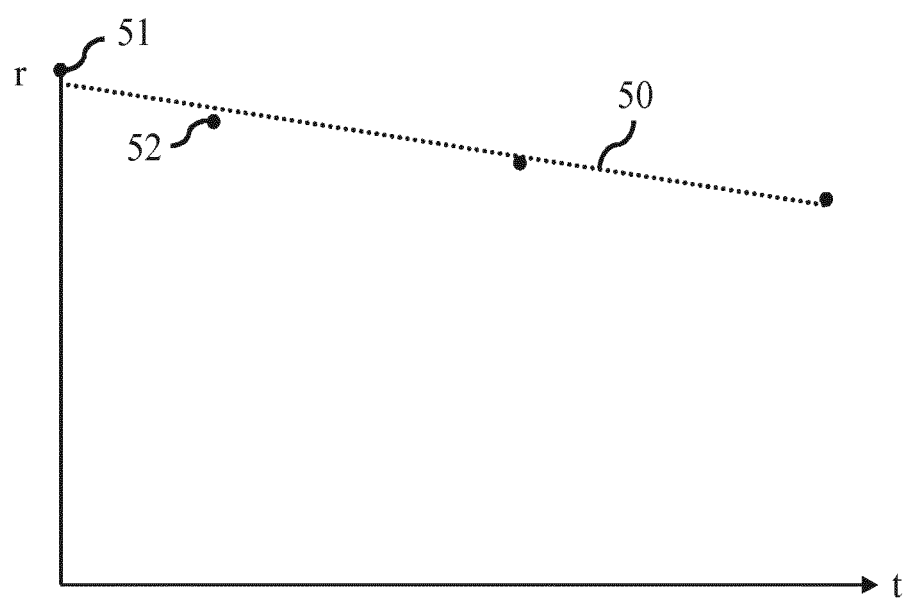
FIG. 5 illustrates a retention factor for Vitamin C concentration of broccoli undergoing a steaming process over time.

FIG. 5 illustrates a retention of Vitamin C concentration for broccoli undergoing a steaming process over time. A retention trendline 50 indicates a line of best fit for the retention factor r over time. As illustrated, a first retention factor 51, measured at a first point in time, is greater than a second retention factor 52, measured at a second, later point in time. Thus, the longer the broccoli is steamed, the smaller the retention factor r.

FIG. 5 therefore illustrates that the retention factor may be determined based on identified processing parameters, here method of processing (steaming) and length of processing (time).

Although preferable, it will be apparent that the nutritional value prediction system need not calculate the nutritional value of the processed food based on quantity data. By way of example, the nutritional value of the processed food may represent a nutritional value per unit weight of the processed food. Alternatively, the food identity data may be used to identify a quantity of the food to be processed. For example, the food identity data may identify that the food to be processed comprises a tin of beans, which may have a fixed quantity or weight.

Examples of processing characteristics which may affect the nutritional value of the processed food will be hereafter described.

In one embodiment, processing characteristics of the kitchen appliance may comprise a length of time for which the food is processed (i.e. an operating time). The length of time for which a food is processed influences the nutrient retention and food weight of the processed food.

In particular, a cooking time of food significantly affects the nutrient loss from the uncooked food to the cooked food. By way of example, a longer cooking time may result in more vitamin loss during cooking.

An operating time of the kitchen appliance may be detected by the appliance characteristic determiner (e.g. tracking how long a certain power supply parameter is ongoing) or based on a known operating mode, such as a present program, of the kitchen appliance.

In an embodiment, processing characteristics of the kitchen appliance may comprise a humidity level of the kitchen appliance when processing the food. The humidity level has also been recognised to influence the nutrient retention and food weight of the processed food.

For example, a cooker (e.g. rice cooker) cooking food using a high humidity is associated with less weight and nutrient loss than a same cooker cooking food using a low humidity.

Processing characteristics of the kitchen appliance may indicate a temperature at which the food is processed. The temperature at which food is processed, e.g. cooked, significantly affects the nutritional value of the processed food.

Processing characteristics of the kitchen appliance may comprise an identity of the kitchen appliance. Different kitchen appliances are associated with different nutritional values of the food following processing.

For example, a first cooker (manufactured by a first manufacturer) and a second cooker (manufactured by a second manufacturer) may be associated with different nutrient losses, even if operating at the same temperature for a same length of time. Such differences may be due to, for example, moisture leakage, fan efficiency, heating characteristics, differing shapes and/or sizes of the cooking area and so on.

Figure 6:
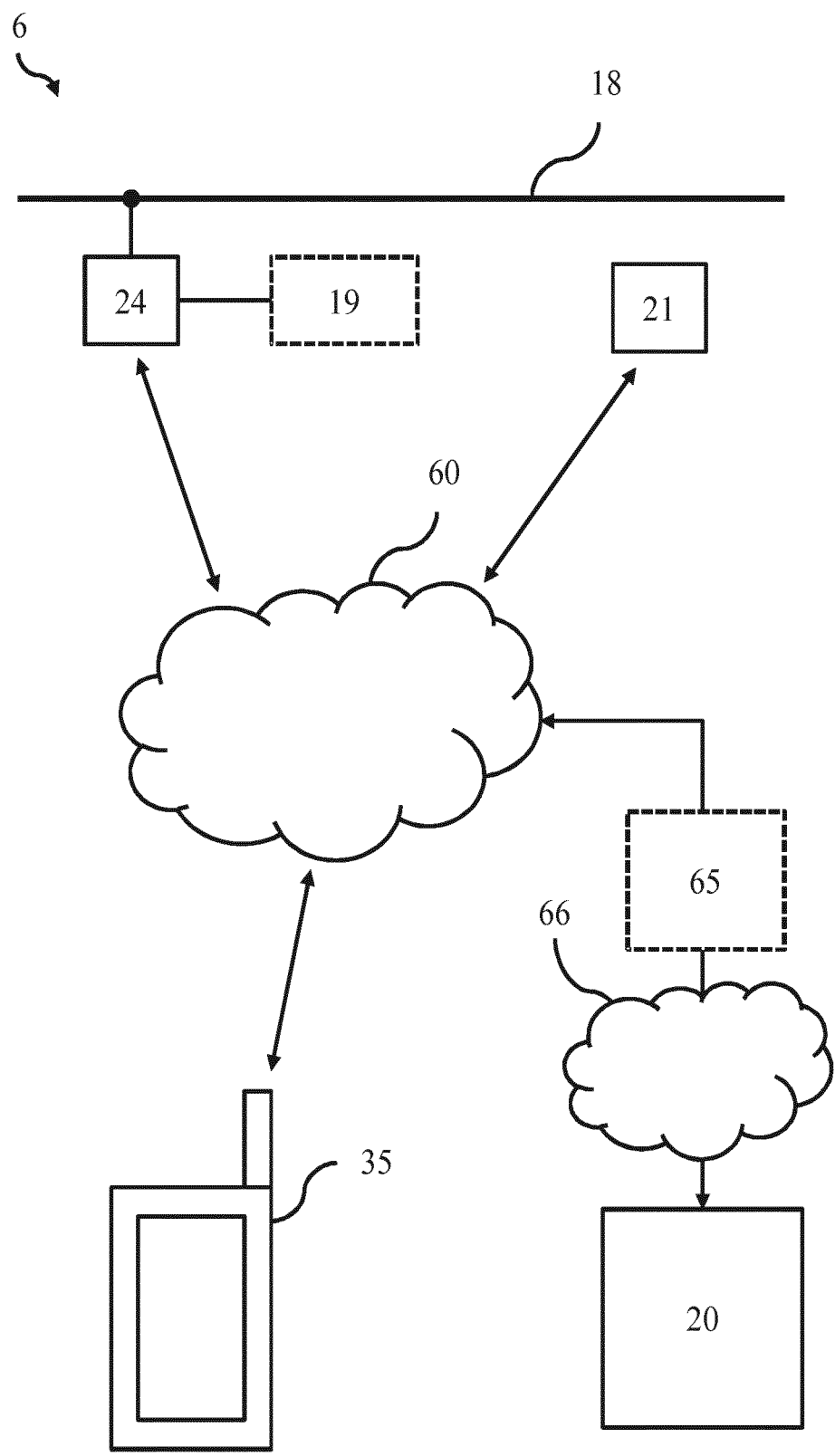
FIG. 6 illustrates a nutritional value prediction system according to another embodiment.

With reference to FIG. 6, a nutritional value prediction system 6 according to an embodiment may employ a distributed computing architecture.

The nutritional value prediction system 6 uses a home network 60 to enable communication between various devices positioned in the home, for example, the food identity determiner 21, the parameter sensor 24 and the user interface arrangement 35.

These devices may communicate with a processing arrangement 20, positioned outside the home network, which predicts the nutritional value and provides the predicted nutritional value to the user interface arrangement 35.

To enable communication between the devices and the processing arrangement 20, the home network 60 may communicate via a router 65, which connects to the internet 66 via an internet service provider. The processing arrangement 20 may thereby be positioned externally to the home or kitchen of a user, for example, in a dedicated server farm or other data processing environment, and communicate via the internet 66.

In another embodiment, rather than communicated exclusively via the home network 60, devices may be adapted to be individually connected to the internet 66 (e.g. via a 3G or 4G communication protocol) in order to communicate with the processing arrangement.

In at least one embodiment, more than one set of processing characteristics, each associated with a different kitchen appliance, may be used to predict the nutritional value of the processed food. Such embodiments recognise that food processed using more than one kitchen appliance would have a different nutritional value to food processed using only one kitchen appliance. For example, if food is initially sliced by a food processor, then cooked in an oven, such processed food would have different nutritional value to food which had only cooked in an oven.

Thus, intermediate data may be stored by a nutritional value prediction system indicating an intermediate step between successive steps of processing according to different processing characteristics (e.g. using different kitchen appliances, or different settings of a same kitchen appliance).

In other embodiments, a nutritional value is calculated for each processing stage (i.e. each instance of using a kitchen appliance). Food identity data may be modified according to the processing characteristics of the kitchen appliance, for example, to identify that food has been chopped using a food processor.

A user may be able to select, using the user interface arrangement 35, which kitchen appliances are used to process the food (e.g. from a list of kitchen appliances identified by the appliance characteristic determiner), and processing characteristics of each selected kitchen appliance may be used to predict a nutritional value of the food successively processed by the kitchen appliances.

Preferably, the user is able to select an order in which the food to be processed is to be processed by the various kitchen appliances.

In one possible alternative, this may be automatically determined by detecting changes to the sensed parameter of the power supply. For example, this may comprise detecting when a blender is switched on, or when an oven door is opened (as a current demand would likely be increased to maintain a temperature of the oven).

It will be apparent that the food identity data may comprise an identity of more than one type of food (e.g. if multiple items of food are to be processed). Similarly, the food quantity data may comprise an indication of the quantity of more than one type of food, preferably each associated with a particular identity of food. Methods and apparatus according to embodiments may process more than one determined nutritional value (e.g. associated with different foods which may potentially be processed in different manners) in order to determine a nutritional value of aggregated food such as a meal.

Other data of the food may also be obtained and used in the prediction of the nutritional value of the processed food, for example, an age of the food a water content of the food and so on.

Various elements of the above described systems may be distributed across one or more devices which may communicate with one another in a variety of ways, for example, using a wireless communication protocol. By way of example, a parameter sensor and a characteristic determination arrangement may be positioned in a same device or in different devices.

Thus, different blocks of the block diagrams of a nutritional value prediction system illustrated by the figures may be variously distributed about different modules or components of the nutritional value prediction system. For example, various blocks illustrated separately may be combined in a single module to advantage or vice versa.

Figure 7:
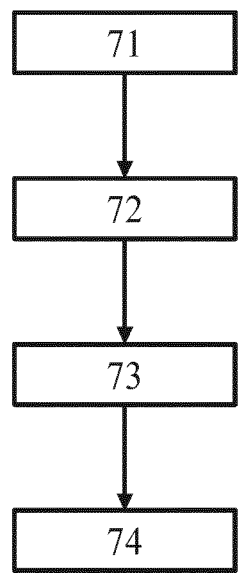
FIG. 7 illustrates a method of predicting a nutritional value of processed food according to an embodiment.

FIG. 7 is a flowchart of a method of predicting a nutritional value of processed food according to an embodiment. The method comprises obtaining 71 food identity data, sensing 72 a parameter of a power supply provided to a kitchen appliance, determining 73 processing characteristics of the kitchen appliance based on the sensed parameter, and predicting 74 a nutritional value of the processed food based on the food identity data and the processing characteristics.

The food identity data is indicative of an identity of the food to be processed by the kitchen appliance, wherein the kitchen appliance is adapted to process food to be processed into processed food.

The processing characteristics are indicative of characteristics of the processing performed by the kitchen appliance and are determined based on the sensed parameter of the power supply.

As discussed above, embodiments make use of a processing arrangement. The processing arrangement can be implemented in numerous ways, with software and/or hardware, to perform the various functions required. A processor is one example of a processing arrangement which employs one or more microprocessors that may be programmed using software (e.g., microcode) to perform the required functions. A processing arrangement may however be implemented with or without employing a processor, and also may be implemented as a combination of dedicated hardware to perform some functions and a processor (e.g., one or more programmed microprocessors and associated circuitry) to perform other functions.

Examples of processing arrangement components that may be employed in various embodiments of the present disclosure include, but are not limited to, conventional microprocessors, application specific integrated circuits (ASICs), and field-programmable gate arrays (FPGAs).

In various implementations, a processor or processing arrangement may be associated with one or more storage media such as volatile and non-volatile computer memory such as RAM, PROM, EPROM, and EEPROM. The storage media may be encoded with one or more programs that, when executed on one or more processors and/or processing arrangements, perform the required functions. Various storage media may be fixed within a processor or processing arrangement or may be transportable, such that the one or more programs stored thereon can be loaded into a processor or processing arrangement.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A nutritional value prediction system for predicting a nutritional value of processed food, wherein the system comprises:
   a food identity determiner adapted to obtain food identity data indicative of an identity of the food to be processed by a kitchen appliance, wherein the kitchen appliance is adapted to process the food to be processed into the processed food;
   an appliance characteristic determiner, comprising a sensor, adapted to:
      detect a parameter of a power supply provided to the kitchen appliance, wherein the parameter of the power supply comprises current supplied to the kitchen appliance;
      determine processing characteristics of the kitchen appliance, indicative of the characteristics of the processing performed by the kitchen appliance, based on the detected parameter of the power supply; and
      identify a type of the kitchen appliance based on the determined processing characteristics of the kitchen appliance and the detected parameter of the power supply, wherein different kitchen appliances have different parameters of the power supply; and
   a nutritional value predictor adapted to determine a nutritional value of the processed food based on the determined processing characteristics of the kitchen appliance, the food identity data, and food weight data indicative of a weight of the food to be processed.

2. The system of claim 1, further comprising a food quantity determiner adapted to obtain food quantity data indicative of a quantity of food to be processed by the kitchen appliance, wherein the nutritional value predictor is adapted to predict the nutritional value of the processed food further based on the food quantity data.

3. The system of claim 1, wherein the appliance characteristic determiner is adapted to:
   sense the current supplied to the kitchen appliance by the power supply; and
   determine the processing characteristics of the kitchen appliance based on the sensed current.

4. The system of claim 1, wherein the appliance characteristic determiner comprises:
   a parameter sensor adapted to detect the parameter of the power supply; and
   a characteristic determination arrangement adapted to receive the detected parameter of the power supply and determine the processing characteristics of the kitchen appliance based on the detected parameter.

5. The system of claim 1, wherein the appliance characteristic determiner is adapted to compare the detected parameter to at least one reference parameter, each of the at least one reference parameter corresponding to different possible processing characteristics of the kitchen appliance, to determine the processing characteristics of the kitchen appliance.

6. The system of claim 1, wherein the appliance characteristic determiner comprises an electrical connector adapted to electrically connect the kitchen appliance to the power supply.

7. The system of claim 1, wherein the processing characteristics of the kitchen appliance comprises one or more of the following: the type of the kitchen appliance; an identity of the kitchen appliance; a model of the kitchen appliance; an operating mode of the kitchen appliance; and an operating parameter of the kitchen appliance.

8. The system of claim 1, wherein the predicted nutritional value comprises one or more of the following: a number of predicted calories of the processed food; a predicted vitamin content of the processed food; a predicted fat content of the processed food, a predicted mineral content of the processed food; a predicted carbohydrate content of the processed food; a predicted sugar content of the processed food; a predicted protein content of the processed food; a predicted fibre content of the processed food; and a predicted salt content of the processed food.

9. A method of predicting a nutritional value of processed food, wherein the method comprises:
   obtaining food identity data indicative of an identity of the food to be processed by a kitchen appliance, wherein the kitchen appliance is adapted to process the food to be processed into the processed food;
   detecting a parameter of a power supply provided to the kitchen appliance, wherein the parameter of the power supply comprises current supplied to the kitchen appliance;
   determining processing characteristics of the kitchen appliance, indicative of the characteristics of the processing performed by the kitchen appliance, based on the detected parameter of the power supply;
   identifying a type of the kitchen appliance based on the determined processing characteristics of the kitchen appliance and the detected parameter of the power supply, wherein different kitchen appliances have different parameters of the power supply; and
   determining a nutritional value of the processed food based on the determined processing characteristics of the kitchen appliance, the food identity data, and food weight data indicative of a weight of the food to be processed.

10. The method of claim 9, further comprising obtaining food quantity data indicative of a quantity of food to be processed by the kitchen appliance, wherein the predicting the nutritional value of the processed food is further based on the food quantity data.

11. The method of claim 10, wherein:
the obtaining the food quantity data comprises obtaining the food weight data indicative of a the weight of the food to be processed.

12. The method of claim 9, wherein the step of detecting the parameter of the power supply comprises sensing the current provided by the power supply to the kitchen appliance.

13. The method of claim 9, further comprising comparing the detected parameter to at least one reference parameter, each of the at least one reference parameter corresponding to different possible processing characteristics of the kitchen appliance, to determine the processing characteristics of the kitchen appliance.

14. A non-transitory computer-readable medium storing software comprising instructions executable by one or more computers which, upon execution, cause the one or more computers to perform the method of claim 9.

* * * * *